United States Patent [19]
Honstein et al.

[11] Patent Number: 5,456,388
[45] Date of Patent: Oct. 10, 1995

[54] THUMBWHEEL OPERATED METERING DISPENSER FOR ADHESIVES

[76] Inventors: Jerry P. Honstein, 6543 Circulo Dali, Anaheim Hills, Calif. 92807; Richard J. Barnes, 23861 Brasilia, Mission Viejo, Calif. 92691

[21] Appl. No.: 125,020

[22] Filed: Sep. 21, 1993

[51] Int. Cl.⁶ .................................................. A61M 5/315
[52] U.S. Cl. ........................ 222/390; 604/225; 604/227; 604/228
[58] Field of Search ................................. 604/218, 220, 604/224, 227, 228; 222/333, 390, 327

[56] References Cited

U.S. PATENT DOCUMENTS

| | | | |
|---|---|---|---|
| 1,556,085 | 10/1925 | De Pew | 604/224 |
| 3,128,765 | 4/1964 | Tint | 604/228 X |
| 3,212,685 | 10/1965 | Swan et al. | 222/390 X |
| 3,281,023 | 10/1966 | Bruck et al. | 222/390 |
| 3,961,731 | 6/1976 | Mochida | 222/390 |
| 4,312,343 | 1/1982 | LeVeen et al. | 604/224 X |
| 4,346,708 | 8/1982 | LeVeen et al. | 604/224 |
| 4,386,606 | 6/1983 | Tretinyak et al. | 604/220 |
| 4,568,335 | 2/1986 | Updike et al. | 604/224 X |
| 4,673,396 | 6/1987 | Urbaniak | 604/224 X |
| 4,810,249 | 3/1989 | Haber et al. | 604/224 X |
| 4,852,768 | 8/1989 | Bartsch | 604/228 X |
| 4,886,188 | 12/1989 | Falco | 222/390 X |
| 5,076,473 | 12/1991 | Steiner | 222/390 X |
| 5,226,895 | 7/1933 | Harris | 604/218 X |

FOREIGN PATENT DOCUMENTS

| | | | |
|---|---|---|---|
| 0223920 | 6/1985 | Germany | 222/390 |
| 8202662 | 8/1982 | WIPO | 604/224 |

*Primary Examiner*—Andres Kashnikow
*Assistant Examiner*—Kenneth Bomberg
*Attorney, Agent, or Firm*—William L. Chapin

[57] ABSTRACT

A hand-held dispenser for delivering small, precisely controllable amounts of fluid or semi-fluid adhesives includes an elongated container having a hollow cylindrical barrel section terminated at the rear end thereof by a pair of diametrically opposed flange wings protruding radially outwards from opposite sides of the barrel, a reduced diameter front tubular outlet section extending forward from the barrel, and a flexible capillary delivery tube protruding outwards from the outlet section. A piston longitudinally slidably located within the bore of the barrel displaces adhesive within the bore forward of the piston by the turning of a lead screw which contacts the rear wall of the piston and which is threadably held within a support member attached to the rear portion of the barrel section. The lead screw is advanceable in precisely controlled small increments by a thumbwheel located rearward of the flange wings, the thumbwheel having a central coaxial perforation that longitudinally slidably receives the lead screw. Rotation of the thumbwheel relative to the lead screw is prevented by contact between a longitudinally disposed flat in the outer surface of the lead screw and a chordal wall that truncates the perforation through the thumbwheel. Thus constructed, the dispenser may be grasped in the fingers of one hand, and the thumb of the same hand used to rotate the thumbwheel and lead screw.

24 Claims, 4 Drawing Sheets

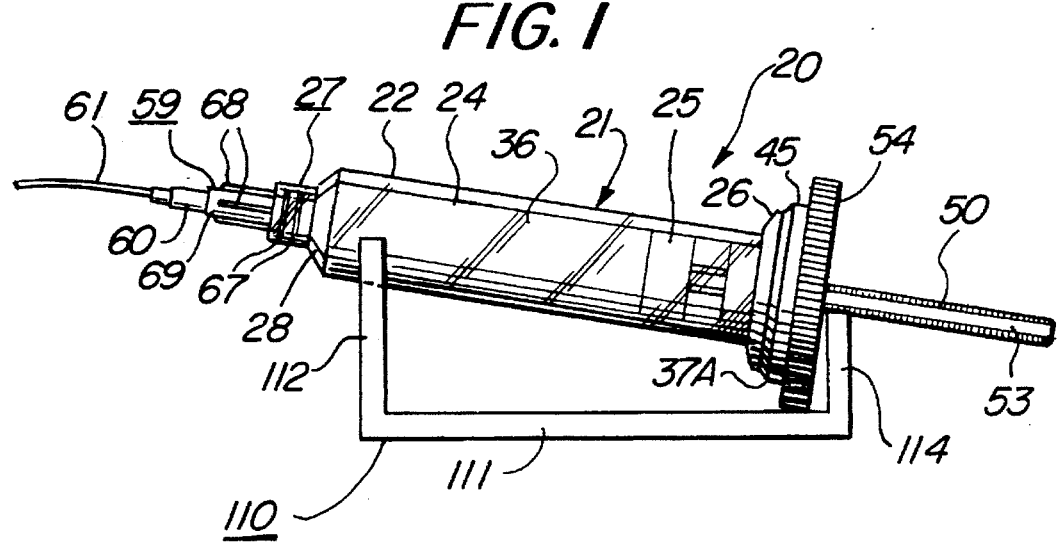
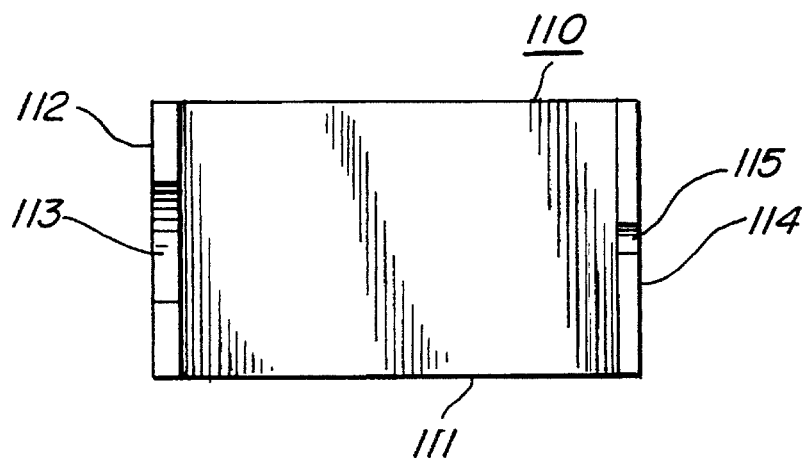
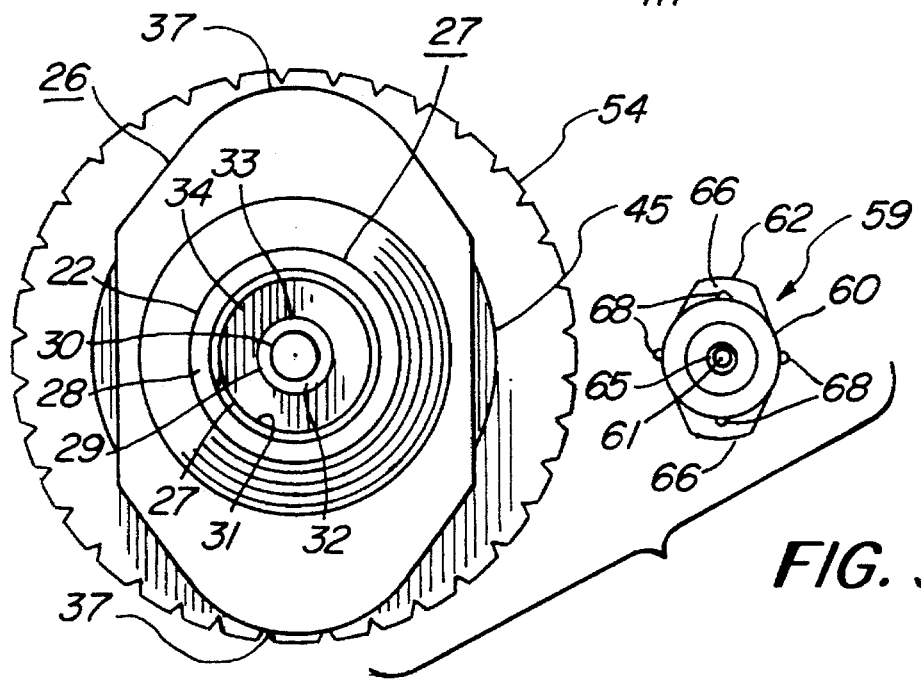

THUMBWHEEL OPERATED METERING DISPENSER FOR ADHESIVES

BACKGROUND OF THE INVENTION

1. Field of the Invention

The present invention relates to dispensers for delivering controlled amounts of fluids. More particularly, the invention relates to a metering dispenser for dispensing precisely controllable small amounts of adhesive to a workpiece.

2. Description of Background Art

A variety of devices adapted to dispense small amounts of fluid adhesives exists. For example, glue jars having a screw cap provided with an attached brush that protrudes downwards into the bottle, have long been known and used. Flexible, squeezable metal or plastic tubes having a small orifice sealed by a screw cap are widely used to dispense various types of adhesives, such as "model airplane" glue containing aromatic hydrocarbons, casein based wood glues, and the like.

One class of adhesives that has become increasingly popular for a wide variety of industrial, commercial and consumer applications is the cyanoacrylates. Cyanoacrylates, which are available as both relatively low viscosity fluids and thicker gels, produce adhesive bonds having a very high tensile strength. For that reason, adhesive bonds formed by cyanoacrylates typically utilize smaller amounts than other types of adhesives. Thus, cyanoacrylate adhesives often are packaged in smaller flexible tubes than are other adhesives, and require a little more finesse in applying adhesive to surfaces to be bonded, since usually only a very small amount of adhesive is required to optimize joint strength.

Besides the requirement for dispensing relatively small amounts of material, dispensers for cyanoacrylates must deal with the problem of clogging of the dispenser delivery orifice. Thus, tubes containing cyanoacrylates, as well as other types of adhesives, usually have a sealed bulkhead under a screw cap, which must initially be pierced with a pin or nail to permit adhesive to be expelled from the tube. After the required amount of adhesive has been dispensed by squeezing the tube, the cap is screwed back on the end of the tube to prevent the adhesive from drying out and hardening. However, owing to the flexibility and shape memory of the tube containing the adhesive, release of squeezing pressure on the tube often results in a re-expansion of the tube. This action draws air through the outlet orifice back into the tube. In the case of cyanoacrylates, oxygen and/or moisture in the air can thicken and harden adhesive within the tube, which must then be prematurely discarded, if the adhesive becomes too hard.

Since cyanoacrylate adhesives form almost instantaneous bonds between a wide variety of materials, including human skin, it would be desireable to provide dispensers for these adhesives that are so constructed as to prevent the possibility of accidental spilling, expelling or squirting adhesive from the dispenser.

Because of the considerations mentioned above, it would also be desirable to have a dispenser for cyanoacrylate adhesives that is capable of delivering small, precisely controllable amounts of adhesive, while eliminating spaces for air above or around adhesive remaining in the dispenser. Although the present inventors are unaware of the existence of any prior art metering dispensers specifically intended to address problems associated with the dispensing of cyanoacrylate adhesives, a number of prior art references disclose dispensers for metering controlled quantities of viscous materials such as dental compositions. These include the following United States patents:

Herold, et al, U.S. Pat. No. 4,479,781, Oct. 30, 1984, Dispenser For Metering Dental Compositions Discloses a one-hand operated dispenser for metering dental compositions that comprises a casing for receiving the dental composition between a forward dispensing end and a plunger which is movably mounted within the casing. The plunger is moved forwardly by means of a threaded spindle which engages with a nut disposed on the rear casing end so as to be secured against rotation and axial movement. The thus formed assembly may be inserted into two bifurcated brackets of a generally U-shaped receptacle forming part of a manipulating member. The spindle is guided in the one bracket so as to be axially movable and non-rotatable, while the casing with the nut is mounted on the other bracket so as to be non-displaceable but rotatable. When the manipulating member is gripped, the casing may be turned between thumb and index finger such that the spindle is pushed forwards, whereby the dental composition exists from the dispensing opening.

The dispenser uses a threaded spindle having a longitudinally disposed flat held irrotational between the two arms of a bifurcated rear bracket forming part of a generally U-shaped receptacle forming part of a "manipulating member," i.e., a handle. A nut threadably holding the spindle is fastened to the rear end of the casing body, which has forward of the nut an annular groove that is held between the two arms of a bifurcated front bracket of the handle. The casing is rotated within the front bracket to cause the threaded spindle to advance into the casing, thereby causing a plunger driven by the front end of the spindle to expel fluid dental composition from the forward dispensing end of the casing.

Neumeister, et al., U.S. Pat. No. 4,560,352, Dec. 24, 1985, Dispenser For Metering Dental Composition Discloses a one-hand operated dispenser for metering dental compositions that comprises a casing for accommodating the dental composition between a forward dispensing opening and a plunger which is slidable within the casing. The plunger is advanced by means of a threaded spindle which engages in a nut mounted at the casing rear end so as to be secured against rotation and axial displacement. The casing rear end is rotatably supported within a sleeve which in turn is detachably inserted in a handle. The sleeve is formed with an axially extending slot through which a finger is visible which is disposed at the rear end of the spindle. When the handle is gripped, the casing may be rotated between the thumb and index finger such that the spindle advances the plunger thereby urging the dental composition out of the dispensing opening. During the forward movement of the spindle the finger travels forwardly in the axially extending slot and indicates the level of the dental composition.

The dispenser uses a rotatable casing, as Herold '781, but uses a threaded spindle without a flat held irrotationally within in a sleeve attached to a handle, a finger protruding radially outward from the end of the spindle held longitudinally slidably but irrotationally within a longitudinally disposed slot in the sleeve.

Vlasich, U.S. Pat. No. 4,641,766, Feb. 10, 1987, Metering Dispenser For High Viscosity Compositions Discloses a dispensing device including a hollow cylindrical body from which a high viscosity composition is discharged in precisely metered doses by a plunger rod longitudinally movable within the body. A series of projections are formed at equi-spaced, longitudinal intervals from each other on the plunger rod. A pair of parallel actuating arms pivotally mounted on the body extend along opposite sides of the plunger rod and are formed with a pair of teeth, respectively, projecting inward toward the rod. By depressing the arms, the teeth pivot into engagement with one of the projections to advance the plunger within the body to expel a desired amount of composition. In a preferred embodiment, advancement of the plunger rod through a precise distance is automatically controlled via contact between the teeth with stop surfaces formed on the next in-line projection.

Vlasich, U.S. Pat. No. 4,658,993, Apr. 21, 1987, Metering Dispenser For Viscous Compositions Discloses a dispensing device which includes a hollow cylindrical body from which a high viscosity composition is discharged in precisely metered doses by means of a plunger rod longitudinally movable within the body. The plunger rod includes a series of thread segments formed at equi-spaced, angular intervals from each other to establish an exterior thread of constant pitch in threaded engagement with the body. Each segment has an abutment surface projecting from the surface of the plunger. By depressing a trigger mounted on the body into contact with an abutment surface aligned therewith, the plunger rotates through the angular interval and thereby advances through the body to expel a desired amount of composition. Disengagement of the trigger with the abutment surface automatically occurs as the abutment surface rotates to the end of the angular interval, out of contact with the trigger, causing the next in-line abutment surface to be indexed into alignment with the trigger to allow for successive doses.

British Patent No. 1,008,505, Quenzer, et al., Nov. 13, 1962, Cylindrical Container With Screw-In Spindle And Piston For Expelling The Contents Through A Frontal Opening Discloses a cylindrical container for dispensing viscous materials which utilizes rotation of a knob attached to the rear end of a spindle threadingly engaged by a cap on the rear end of the cylinder to advance a piston contacted by the front end of the spindle, thereby expelling material from an opening in the front end wall of the cylinder.

German Patent No. 223,920, Jun. 26, 1985, Tube Filling Appliance

Discloses a tube filling Appliance for the dosage, filling and application of ointments or substances of similar viscosity in pharmaceutical dispensaries under sterile conditions that consists of a glass cylinder with a filler tube in which a piston can be moved by a feedscrew.

A handwheel attached to the end of the feedscrew is turned to move the piston forward. The device includes a stand that is equipped with a suction cup type of footing. The glass cylinder is laid in the stand affixed by a bayonet joint of the cap.

The tube to be filled (e.g., an aluminum tube for eye ointment) is pushed over the filler tube.

The present invention was conceived to provide an improved dispenser for metering small amounts of fluid material, the dispenser being particularly well adapted to dispensing cyanoacrylate adhesives.

OBJECTS OF THE INVENTION

An object of the present invention is to provide a metering dispenser for dispensing small, precisely controllable quantities of fluid or semi-fluid materials.

Another object of the invention is to provide a metering dispenser for fluids that is holdable and operable in one hand.

Another object of the invention is to provide a hand-held metering dispenser for fluids that includes a flexible outlet tube.

Another object of the invention is to provide a metering dispenser for adhesives that is adapted to be held and operated in one hand by rotation of a lead screw to dispense precisely and continuously controllable quantities of adhesive.

Another object of the invention is to provide a metering dispenser for adhesives that utilizes a lead screw driven piston within a cylinder that can remain fixed with respect to application point of adhesive.

Another object of the invention is to provide a lead screw actuated metering dispenser for adhesives that utilizes an unmodified syringe body.

Various other objects and advantages of the present invention, and its most novel features, will become apparent to those skilled in the art by perusing the accompanying specification, drawings and claims.

It is to be understood that although the invention disclosed herein is fully capable of achieving the objects and providing the advantages described, the characteristics of the invention described herein are merely illustrative of the preferred embodiments. Accordingly, we do not intend that the scope of our exclusive rights and privileges in the invention be limited to details of the embodiments described. We do intend that equivalents, adaptations and modifications of the invention reasonably inferable from the description contained herein be included within the scope of the invention as defined by the appended claims.

SUMMARY OF THE INVENTION

Briefly stated, the present invention comprehends an improved hand-held metering dispenser for delivering small, precisely controllable amounts of fluid or semi-fluid materials, particularly cyanoacrylate adhesives, to a desired location on a surface of an object to be adhesively bonded.

The dispenser according to the present invention includes an elongated, hollow, cylindrical syringe barrel having a reduced diameter front tubular section to which is attached a flexible, smaller bore delivery tube. The barrel is filled with liquid adhesive, closed off at the rear end by a piston slidable within the barrel. A support member attached to the rear of the barrel contains a central coaxial threaded through-hole which threadingly engages an elongated threaded spindle or lead screw. One type of support member has a cylindrical portion that is press fitted or screwed into the rear circular opening of the syringe barrel. Another type of support member consists of a block provided with a slot adapted to insertingly receive flange wings protruding transversely outwards from opposite sides of the rear end of the syringe barrel, the block having a rear wall provided with a coaxial threaded bore adapted to receive a lead screw.

The dispenser includes a lead screw that has formed on the outer surface thereof at least one longitudinally disposed flat that runs the length of the lead screw. A thumbwheel having a central coaxial aperture shaped complementarily to the cross-sectional shape of the lead screw fits slidably over the lead screw, but is irrotational with respect to the lead screw. Rotating the thumbwheel with respect to the syringe barrel and insert causes the lead screw to move threadingly forward, thus exerting a forward directed compression force on the rear wall of the piston, thereby causing precisely controllable amounts of adhesive to be expelled from the flexible delivery tube. Thus constructed, the barrel of the dispenser may be gripped between as few as two fingers of one hand to hold the tip of the flexible delivery tube adjacent an intended delivery point, while the thumbwheel may be rotated by thumb pressure alone to expel precisely controllable amounts of adhesive.

BRIEF DESCRIPTION OF THE DRAWINGS

FIG. 1 is a side elevation view of a thumbwheel operated metering dispenser according to the present invention, showing the dispenser held in a stand.

FIG. 2 is an upper elevation view of the stand of FIG. 1.

FIG. 3 is a fragmentary front elevation view of the dispenser of FIG. 1, showing a syringe body and disassembled tip comprising part of the dispenser.

DESCRIPTION OF THE PREFERRED EMBODIMENTS

Figure 4:
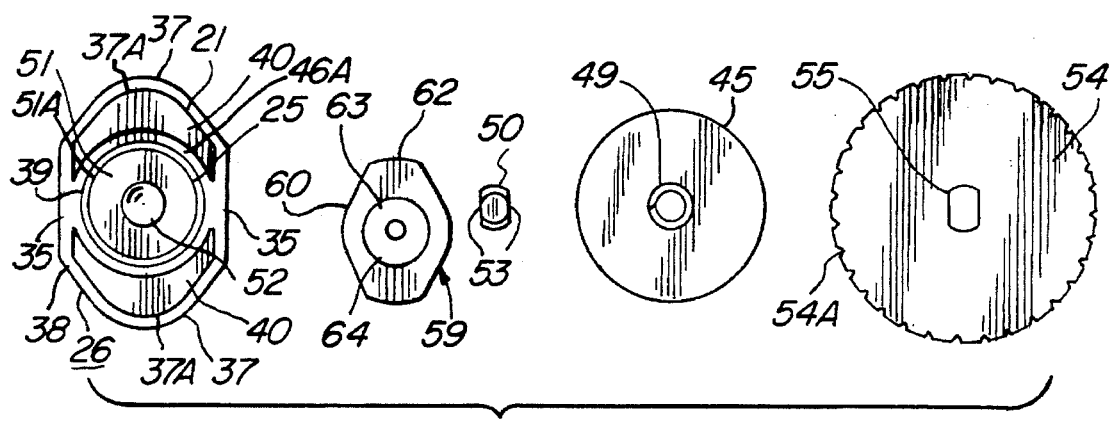
FIG. 4 is a rear elevation view of the syringe body, tip, lead screw, thumbwheel, and a lead screw-supporting insert comprising parts of the dispenser of FIG. 1.

Referring now to FIGS. 1 through 10, a thumbwheel operated metering dispenser for adhesives is shown.

As shown in FIG. 1, dispenser 20 according to the present invention includes a body 21 including an elongated cylindrical barrel 22, the hollow cylindrical interior space or bore 23 of which contains a column of fluid or semi-fluid adhesive 24. A cylindrical piston 25 fits slidably within bore 23 of barrel 22, and is in sealing peripheral contact with the inner cylindrical wall surface 75 of the barrel, and in abutting contact with the rear circular face of adhesive column 24.

As shown in FIG. 1, barrel 22 of dispenser 20 has an elongated cylindrically shaped main or central section 22A, a transversely disposed rear flange 26, and a reduced diameter front tubular section or neck 27 coaxial with the central section and joined thereto by a frustoconically-shaped annular front wall or shoulder 28.

As may be seen best by referring to FIGS. 1 and 3, neck 27 encircles a smaller diameter, hollow outlet tube 29 joined to the neck near the smaller diameter, upper end of the shoulder by a thin annular flange wall 30 disposed between the inner cylindrical wall surface 31 of the neck and the outer cylindrical wall surface 32 of the outlet tube. Preferably, as shown in FIG. 1, the front or outer annular wall 33 of outlet tube 29 protrudes a short distance longitudinally outwards beyond the front annular wall 34 of neck 27.

As may be seen best by referring to FIGS. 1 and 4, rear flange section 26 of dispenser 20 has flat parallel side walls 35 that protrude short, equal distances laterally outwards from the outer cylindrical wall surface 36 of dispenser barrel 22. Flange 26 also has longer, oval-shaped symmetrical upper and lower side walls 37 that protrude symmetrically outwards from outer wall surface 36 of barrel 22 a greater distance than side walls 35, forming a pair of transversely disposed wings 37A.

As may be seen best by referring to FIG. 4, flange 26 has a longitudinally rearwardly protruding peripheral wall 38 of generally uniform thickness and width. Peripheral wall 38 encircles and is centrally joined to rear annular wall 39 of barrel 21, forming therebetween a pair of upper and lower, symmetrical, crescent-shaped depressions 40. As may be seen best by referring to FIG. 5, flange 26 has a front wall 42 that is tapered radially outward to a smaller outer thickness in the vicinity of wings 37A.

As so far described, body 21 of dispenser 20 has the construction and appearance of a hypodermic syringe body. In the preferred embodiment, body 21 is fabricated by injection molding from a synthetic polymer such as high-density polyethylene.

Figure 5:
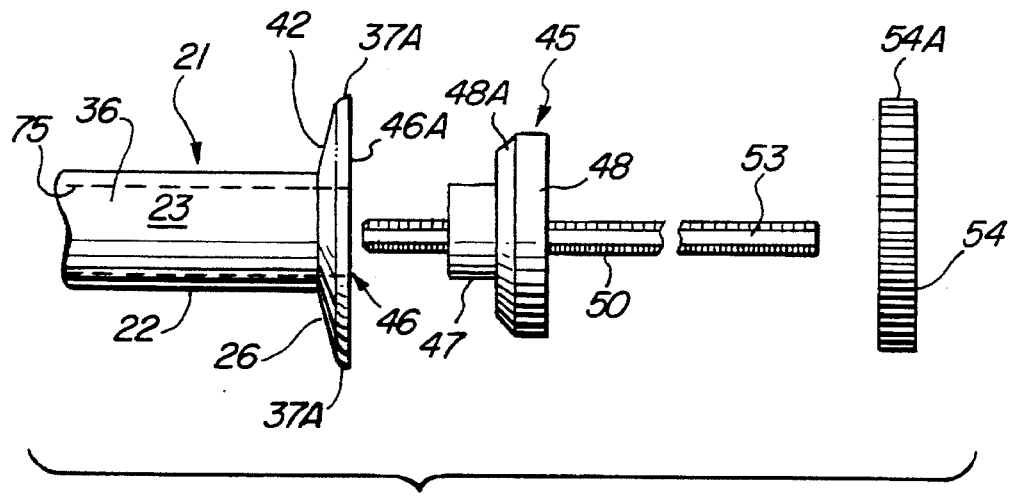
FIG. 5 is a side elevation view of the insert comprising part of the dispenser of FIG. 1.
Figure 6:
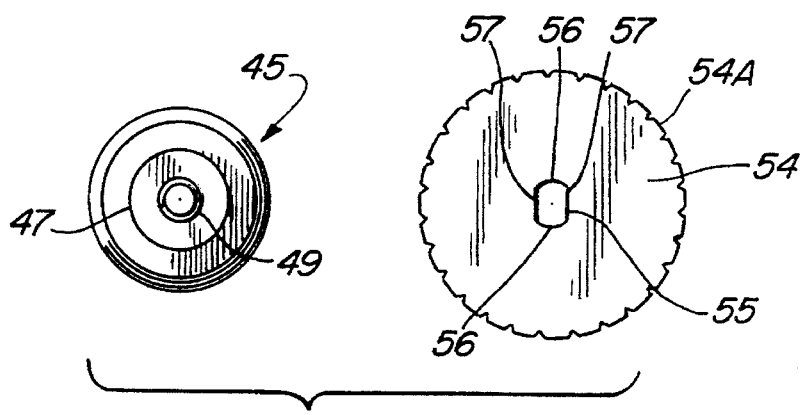
FIG. 6 is a front elevation view of the insert of FIG. 5.

Referring again to FIGS. 1 and 4 through 6, dispenser 20 may be seen to include a lead screw support member including an insert 45 which fits tightly into rear opening 46 of barrel 22. As shown in FIGS. 1 and 4, insert 45 has a front cylindrical section 47 adapted to be insertably received into rear opening 46 of barrel 22, and an enlarged diameter rear section 48 coaxial with front section 47. A central coaxial threaded bore 49 runs through the entire length of insert 45. As shown in FIGS. 4 through 6, rear opening 46 of barrel 22 preferably has a chamfered entrance 46A, and rear section 48 of insert 45 has a front chamfered section 48A shaped complementarily to chamfer 46A, thus adapting the insert to seat firmly in entrance opening 46.

As shown in FIG. 1, dispenser 20 includes an elongated, externally threaded spindle or lead screw 50 that is threadingly engaged within threaded bore 49 of insert 45. The front transverse end of lead screw 50, which is preferably convexly curved, bears against the rear wall surface 51 of piston 25 slidably contained within barrel 22. Preferably, as shown in FIG. 4, rear wall surface 51 of piston 25 is provided with a coaxially centered, cup-shaped depression 52, adapted to receive and center lead screw 50.

Referring still to FIGS. 1 and 4, lead screw 50 may be seen to have formed in the outer wall surface thereof a pair of diametrically opposed longitudinally disposed flats 53. That portion of lead screw 50 that protrudes rearward from barrel 22 and insert 45 of dispenser 20 is insertably received by a thin circular disk-shaped thumbwheel 54. As shown in FIG. 4, thumbwheel 54 has through its thickness dimension a central perforation or hole 55 having an outline shape complementary to the transverse cross-sectional shape of lead screw 50. Thus, hole 55 has symmetrical, semi-circularly shaped upper and lower walls 56, and a pair of straight parallel side walls 57. This construction allows thumbwheel 54 to slide freely in a longitudinal direction on lead screw 50, while preventing relative rotation between those two parts. Accordingly, lead screw 50 and piston 25 may be advanced longitudinally with respect to insert 45 and barrel 22 of dispenser 20 by rotating thumbwheel 54 with respect to the barrel. Since piston 25 exerts hydrostatic pressure on adhesive 24 in bore 23 of barrel 22, this action causes precisely controllable amounts of adhesive to be expelled through bore 58 of small diameter outlet tube 29 located at the front of barrel 22.

In the preferred embodiment, dispenser 20 includes a tip having a flexible tube for delivering adhesive expelled from outlet tube 29 to a surface. Thus, as shown in FIGS. 1, 3 and 4, dispenser 20 preferably includes a tip 59 having an elongated generally cylindrically-shaped hollow rear body section 60, and a flexible capillary delivery tube 61 protruding forward from the rear body section. Rear body section 60 has a transversely disposed rear flange wall 62. A central coaxial bore 63 extends forward through flange wall 62 and a substantial portion of rear body section. Bore 63 is of the proper diameter and length to insertably receive outlet tube 29 of dispenser body 21. Bore 63 communicates at its front end with tapered section 64 that in turn communicates with a short front entrance bore 65. Front entrance bore 65 of rear body section 60 insertably receives flexible capillary delivery tube 61 which is attached to the rear body section by an interference fit. Preferably, flexible delivery tube 61 is made of a synthetic polymer that has a high surface lubricity which resists bond formation with adhesives expelled through the tube. Thus, suitable materials for flexible delivery tube 61 are polytetrafluoroethylene (TFE TEFLON®) or fluorinated ethylene propylene (FEP TEFLON®).

As shown in FIGS. 1, 3 and 4, tip 59 is preferably attached to body 21 of dispenser 20 by threadingly engaging upper and lower wing sections 66 of flange wall 62 with internal helical threads 67 formed in inner cylindrical wall surface 31 of neck 27. Preferably, a plurality of circumferentially spaced apart, longitudinally disposed raised ribs 68 are formed in the outer portion of cylindrical wall 69 of rear section 60 of tip 59. Ribs 68 provide a gripping surface that facilitates applying sufficient torque on rear section 60 of tip 59 to screw flange wings 66 tightly into threads 67 of neck 27, thereby causing front annular wall 33 of outlet tube 29 to butt firmly and sealingly against tapered front section 64 of bore 63 through the rear section of the tip.

Figure 7:
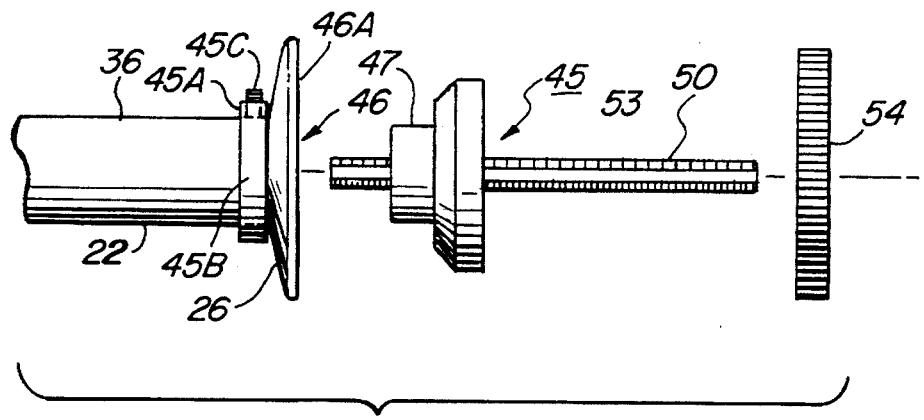
FIG. 7 is a side elevation view of a modification of the insert of FIGS. 5 and 6.
Figures 8, 9, 10:
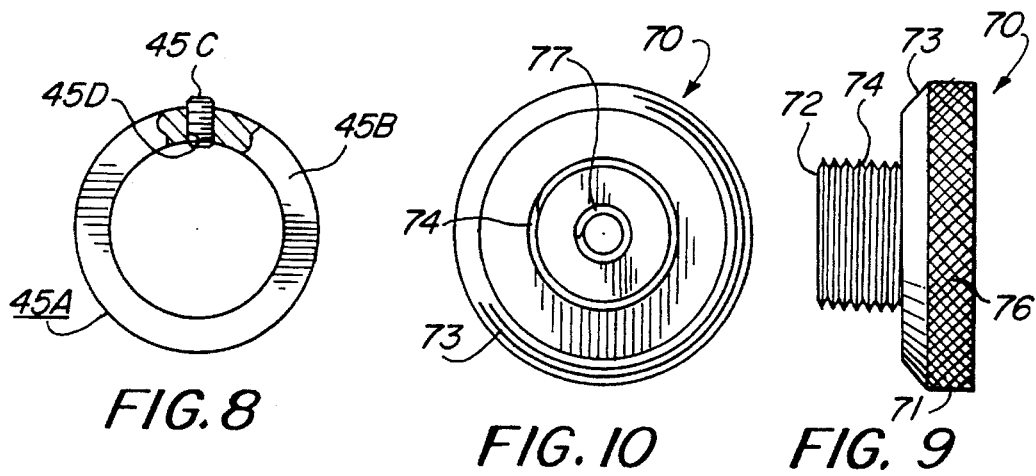
FIG. 8 is a rear elevation view of the modification of FIG. 7.
FIG. 9 is a side elevation view of a second embodiment of an insert for use in the dispenser of FIG. 1.
FIG. 10 is a front elevation view of the insert of FIG. 7.

FIGS. 7 and 8 illustrate a clamp used to hold the insert shown in FIGS. 5 and 6 more securely within barrel 22. As shown in FIGS. 7 and 8, clamp 45A consists essentially of an annular ring 45B threadingly holding a set screw 45C in a threaded bore 45D disposed radially through the ring. Ring 45B is made of a relatively rigid material such as metal or plastic, and has an inner diameter of the proper size to fit snugly on the outer cylindrical wall surface 36 of barrel 22.

As shown in FIGS. 7 and 8, ring 45B is slid rearward over dispenser barrel 22 sufficiently far to abut the front surface of rear flange 26. After front cylindrical section 47 of insert 45 has been press fitted into rear opening 46 of barrel 22, set screw 45C is screwed into threaded bore 45D of ring 45B sufficiently far to compress the barrel slightly, thus exerting a radially inwardly directed compressive clamping force on the cylindrical section of the insert.

FIGS. 9 and 10 illustrate a second embodiment of an insert for use with the dispenser of FIGS. 1 through 4. As shown in FIGS. 9 and 10, insert 70 is shaped similarly to insert 45, shown in FIGS. 5 and 6 and described above. Thus, insert 70 has a cylindrically shaped rear section 71, and a smaller diameter front cylindrically shaped section 72. Preferably, the front circular surface of rear section 71 has a chamfer 73 adapted to seat within chamfer 46A of rear opening 46 of dispenser barrel 22. As may be seen best by referring to FIG. 9, the outer cylindrical wall surface of front section 72 of insert 70 has formed therein external helical threads 74. Threads 74 preferably have a relatively sharp longitudinal cross-sectional shape that adapts the threads to self-thread into the inner cylindrical wall surface 75 of barrel 22. Also, the outer annular surface of rear section 71 of insert 70 preferably has formed therein knurls 76, to facilitate screwing the insert into barrel 22. As shown in FIG. 10, insert 70 also has through its thickness dimension a central coaxial threaded bore 77, adapted to threadingly receive lead screw 50.

Figure 11:
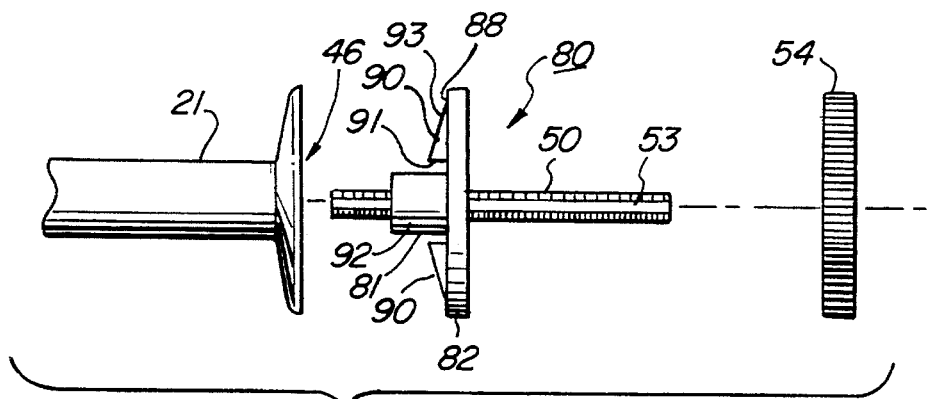
FIG. 11 is a side elevation view of a third embodiment of an insert for use in the dispenser of FIG. 1.
Figure 12:
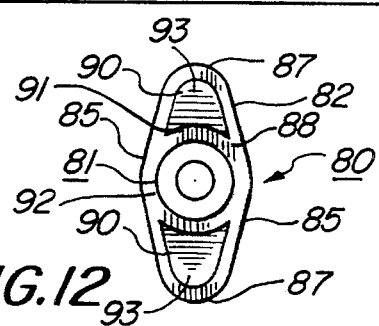
FIG. 12 is a front elevation view of the insert of FIG. 9.

FIGS. 11 and 12 illustrate a third embodiment of an insert for use with the dispenser of FIGS. 1 through 4. As shown in FIGS. 11 and 12, insert 80 has a front cylindrically-shaped section 81 adapted to be insertably received into rear opening 46 of dispenser barrel 22, and be held in an interference fit within bore 23 of the barrel. Insert 80 also has a rear transverse wall section 82 of generally uniform thickness concentric with front cylindrically-shaped section 81. As may be seen best by referring to FIG. 12, rear section 82 has approximately the same size and transverse cross-sectional shape as rear flange wall 26 of dispenser body 20. Thus, rear transverse wall section 82 has the approximate shape of a flattened oval having a pair of slightly curved symmetrical side edge walls 85, and a pair of symmetrically-shaped upper and lower arcuately curved convex edge walls 87 having greater curvature than the side walls.

Insert 80 has protruding forward from front surface 88 of rear transverse wall section 82 a pair of symmetrically-shaped lugs 90 positioned symmetrically above and below front cylindrical section 81 of the insert. As shown in FIG. 12, the transverse cross-sectional shape of lugs 90 is similar to that of crescent-shaped depression 40 in rear flange wall 26 of dispenser body 21, as shown in FIG. 4, thus adapting the lugs to be insertably received by the depressions when front cylindrical section 81 is forcibly inserted into rear opening 46 of barrel 22. As shown in FIG. 11, lugs 90 preferably have in longitudinal section a generally wedge shape. Thus, each lug 90 has a relatively thick upper edge wall 91 concentric with and spaced radially outwards from the outer cylindrical wall surface 92 of front cylindrical section 81, and an obliquely disposed front wall 93 that tapers radially outwards to join front surface 88 of rear transverse wall section 82. Thus constructed, lugs 90 are adapted to fit conformally into depressions 40 of rear flange wall 26 of dispenser barrel 22, when insert 80 is press fitted into the barrel. In this position, the sloping front walls of lugs 90 contact complementary-shaped sloping rear walls 41 of the depressions. With lugs 90 lockingly received in depressions 40, any tendency of insert 80 to rotate along with lead screw 50 when the lead screw is turned to expel adhesive is prevented.

FIGS. 13 through 17 illustrate an alternate embodiment of lead screw support member for attachment to dispenser body 21.

Figure 13:
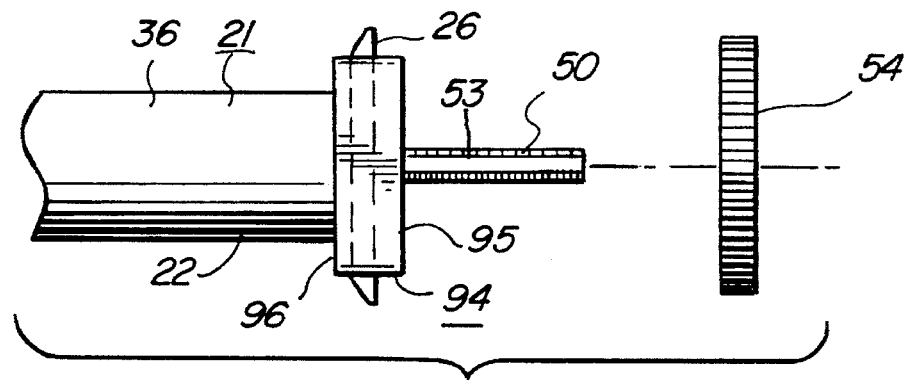
FIG. 13 is a side elevation view of an alternate embodiment of a lead screw supporting member for use with the dispenser of FIG. 1.
Figure 14:
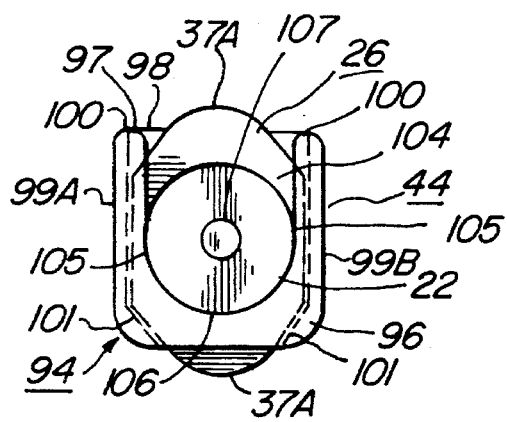
FIG. 14 is a front elevation view of the supporting member of FIG. 13.
Figure 15:
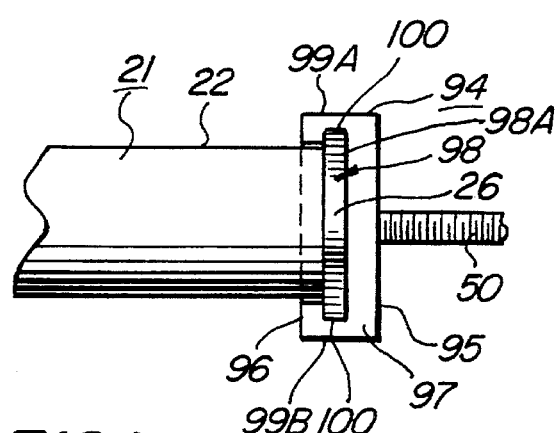
FIG. 15 is an upper plan view of the support member of FIG. 13.
Figure 16:
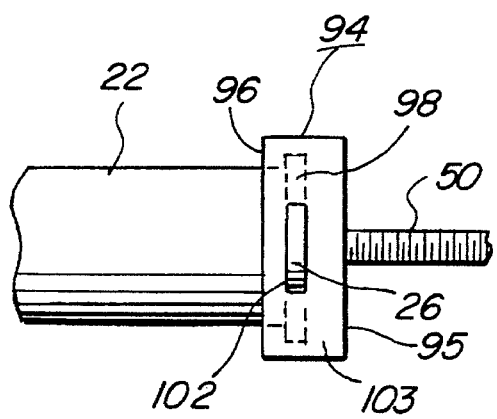
FIG. 16 is a bottom plan view of the support member of FIG. 13.

As shown in FIGS. 13 through 17, lead screw support member 94 slidably attaches to rear flange 26 of dispenser body 21. As shown in FIGS. 13, 15 and 16, slidably attachable lead screw support member 94 has in side elevation view the shape of a rectangular block having a longitudinal thickness and width greater than that of rear dispenser flange 26, and a height less than that of the rear flange. As may be seen best by referring to FIGS. 17 and 14, lead screw support member 94 has a flat, rectangularly shaped rear wall 95, and a front wall 96 of the same general outline shape spaced forward of the rear wall. As may be seen best by referring to FIG. 15, support member 94 has a flat upper wall 97 in which is formed a wide, thin slot 98 which extends downward into the member. Slot 98 extends symmetrically outwards toward side walls 99A and 99B of the support member. As shown in FIGS. 14, 15 and 16, slot 98 has vertical side walls 100 and obliquely inwardly disposed lower walls 101 that taper to a smaller width rectangular perforation 102 in bottom wall 103 of the member 94.

As may be seen best by referring to FIG. 14, front wall 96 of lead screw support member 94 has formed therein a generally rectangularly shaped notch 104 which extends downwards from upper wall 97 of the support member. Notch 104 has parallel vertical side walls 105, and an arcuately curved, concave bottom wall 106.

Figure 17:
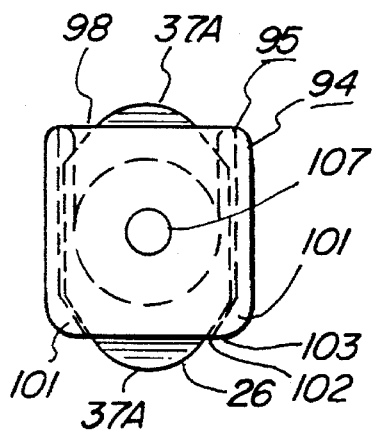
FIG. 17 is a rear view of the support member of FIG. 13.

As may be seen best by referring to FIGS. 14 and 17, rear wall 95 of lead screw support member 94 has through the thickness dimension thereof a threaded bore 107 adapted to threadingly receive a lead screw 50.

Support member 94 is attached to dispenser body 21 by positioning opening 98A of slot 98 in upper wall 97 of the support member parallel to and transversely aligned with a lower wing 37A of flange 26 of the dispenser body. Then, as shown in FIGS. 14 and 17, an adjacent wing 37A is inserted into opening 98 of slot 98, and the dispenser body 21 and support member 94 moved transversely with respect to one another to seat one side of outer cylindrical wall surface 36 of dispenser barrel 22 against arcuately curved lower wall 106 of notch 104 in front wall 96 of the support member. Since lower wall 106 is concentric with threaded bore 107 through rear wall 95 of support member 94, and has the same curvature as dispenser barrel 22, seating the dispenser barrel on curved lower wall 106 aligns the threaded bore with the longitudinal axis of the dispenser barrel. Referring now to FIGS. 13, 15 and 16, with support member 94 thus positioned relative to dispenser barrel 22, lead screw 50 is screwed into threaded bore 107 through rear wall 95 of the support member sufficiently far for the front end of the lead screw to be insertably received by centering depression 52 in rear wall 51 of piston 25, as shown in FIG. 1.

As was stated above, body 21 of dispenser may be made of any suitable rigid material, but is preferably fabricated as an injection molded part from polyethylene or similar thermoplastic. For reasons previously stated, flexible delivery tube 61 of dispenser 20 is preferably fabricated from TFE or FEP. Although piston 25 may be made from materials similar to those listed above, we have found that, for use with cyanoacrylate adhesives, piston 25 should be made of a high density polyethylene.

Also, rear wall surface 51 of piston 25 preferably has a thin peripheral annular region or skirt 51A that helps to prevent rearward leakage of adhesive 24 past the piston within bore 23 of dispenser 20.

To use dispenser 20, barrel 22 of the dispenser is gripped between any convenient combination of two or more fingers, with the thumb of the same hand placed adjacent knurled outer peripheral surface 54A of thumbwheel 54. Tangential forces may then easily be exerted by the thumb on surface 54A of the thumbwheel, producing a torque that causes the thumbwheel and lead screw 50 to be rotated with respect to barrel 22 of dispenser. Because of the novel construction of dispenser 20, thumbwheel 54 and lead screw 50 may be rotated in increments as small as desired, advancing piston 25 to expel liquid adhesive 24 in amounts as minute as desired. Since barrel 22 of dispenser 20 is held in a fixed non-rotating relationship relative to a work surface when thumbwheel 54 is rotated to expel adhesive, flexible capillary delivery tube 61 is held immobile with respect to the work surface, even if the tube is bowed, as occurs commonly with flexible tubes. It is also important to note that the lead screw mechanism used to expel adhesive from dispenser barrel 22 has no tendency to reverse direction upon removal of actuating torque on thumbwheel 54. Therefore, negative pressure within delivery tube 61, which could draw air or moisture back into the dispenser, is prevented from occurring. Also, the novel dispenser construction according to the present invention precludes the possibility of any accidental leakage or spilling of adhesive from the dispenser, or any accidental forceable ejection of adhesive that could pose a safety or health hazard.

In the preferred embodiment of dispenser 20, a stand is used to support the dispenser when it is not in use. Thus, as shown in FIGS. 1 and 2, dispenser 20 preferably includes a stand 110 having a flat base 111 adapted to rest on a flat surface such as that of a table or bench, and a front upright member 112 protruding upright from the front edge of the base and having in its upper edge wall an arcuately curved notch 113 adapted to support the outer cylindrical wall of barrel 22 of the dispenser. Stand 110 includes a rear upright member 114 of less height than front upright member that protrudes upwards from the rear edge of base 111. Rear upright member 114 has formed in the upper edge wall thereof an arcuately curved notch 115 adapted to cradle lead screw 50, rearward of thumbwheel 54.

What is claimed is:

1. A dispenser for ejecting controllable amounts of fluid comprising:
   a. an elongated, hollow cylindrical container having a smooth bore communicating near a first, front transverse end thereof with an outlet orifice, said container having a circular rear opening coextensive with said bore,
   b. a piston longitudinally slidably located within said bore of said container, said piston forming within said container between a front face of said piston and said outlet orifice a hollow interior space for containing a fluid, and
   c. means for advancing said piston forward in said container, thereby displacing a quantity of fluid contained within said container through said outlet orifice, said advancing means comprising in combination;
      (i) an elongated threaded member disposed longitudinally within said container and contacting a rear face of said piston,
      (ii) a support member attached to said container rearward of said piston, said support member having therethrough a threaded hole threadingly receiving said elongated threaded member, and
      (iii) a rotatable member for turning said elongated threaded member about a longitudinal axis thereof, thereby threadingly advancing said threaded member and said piston forward with respect to said support member, said rotatable member having a longitudinally disposed perforation therethrough adapted to permit freely slidable movement of said elongated threaded member through said rotatable member, said rotatable member having means making said rotatable member irrotational with respect to said elongated threaded member, whereby torque applied to said rotatable member is transmitted to said elongated threaded member, thereby advancing said elongated threaded member through said rotable member and into said container.

2. The dispenser of claim 1 wherein said elongated threaded member is further defined as having formed on an outer surface thereof at least one longitudinally disposed flat.

3. The dispenser of claim 2 wherein said means for making said rotatable member irrotational with respect to said elongated threaded member is further defined as a protrusion extending radially inwards from a circumferential surface defining at least part of an inner peripheral wall surface of said longitudinally disposed perforation through said rotatable member, said protrusion contacting said flat.

4. The dispenser of claim 3 wherein said protrusion is further defined as a chordal flat formed in an otherwise generally circular perforation through said rotatable member.

5. The dispenser of claim 3 wherein said protrusion is further defined as a set screw threadingly engaged in a radially disposed threaded bore communicating with said longitudinally disposed perforation through said rotatable member.

6. The dispenser of claim 1 wherein said support member is further defined as being a longitudinally elongated body having a front cylindrically-shaped section adapted to be insertably received into said circular rear opening of said bore of said container, said threaded hole through said support member being disposed coaxially and longitudinally through said body.

7. The dispenser of claim 6 wherein said cylindrical front section of said support member is adapted to be press fitted into said bore of said container.

8. The dispenser of claim 6 wherein said cylindrical front section of said support member has oh the external cylindrical surface thereof threads adapted to threadingly engage the inner cylindrical wall surface of said container.

9. A dispenser for delivering controllable amounts of fluid to a surface comprising;
   a. a container body having an elongated, hollow cylindrical barrel section having therethrough a cylindrical bore communicating with a circular rear opening, a coaxial hollow tubular front section of smaller diameter than said barrel section and having an outlet orifice in communication with said bore, and a transversely disposed rear flange adjacent said circular rear opening of said barrel, said flange having formed therein a pair of diametrically opposed, flat semi-oval wing sections protruding transversely outwards from opposite outer cylindrical wall surfaces of said barrel,
   b. a cylindrically shaped piston longitudinally slidably located within said bore of said barrel section of said container body, said piston forming within said barrel section between a front face of said piston and said hollow tubular front section a hollow interior space for containing a fluid, and
   c. means for advancing said piston longitudinally forward within said barrel, thereby displacing a quantity of fluid contained within said barrel through said outlet orifice of said hollow tubular front section, said advancing means comprising in combination;
      (i) a support member attached to the rear portion of said barrel section, said support member having therethrough a longitudinally disposed threaded hole,
      (ii) an elongated threaded member disposed longitudinally within said barrel and threadingly engaged within said longitudinally disposed threaded hole of said support member, and
      (iii) a thumbwheel for turning said elongated threaded member about a longitudinal axis thereof, thereby advancing said threaded member and said piston forward with respect to said support member, said thumbwheel having therethrough a longitudinally disposed perforation adapted to permit freely slidable longitudinal movement of said elongated threaded member through said thumbwheel, said thumbwheel including keying means holding said threaded member irrotational with respect to said thumbwheel, whereby torque produced by application of a tangential force to said thumbwheel by the thumb produces a torque effective in turning said threaded member about its longitudinal axis.

10. The dispenser of claim 9 wherein said keying means is further defined as comprising in combination a non-circular cross-sectional shape formed in a longitudinally disposed portion of said elongated threaded member, and a complementary non-circular cross-sectional shape formed in said perforation through said thumbwheel.

11. The dispenser of claim 10 wherein each of said complementary cross-sectional shapes is defined as a circle modified by a chordal flat.

12. The dispenser of claim 10 wherein each of said complementary cross-sectional shapes is further defined as being a circle modified by a pair of circumferentially spaced apart chordal flats.

13. The dispenser of claim 9 wherein said support member is further defined as being a fitment attachable to said container body, said fitment including means for attaching said fitment to said container body with said longitudinally disposed hole through said fitment positioned in coaxial alignment with said bore of said barrel section of said container body.

14. The dispenser of claim 9 wherein said support member is further defined as being a longitudinally elongated body having a front cylindrically-shaped section adapted to be insertably received into said rear circular opening of said barrel section of said container body.

15. The dispenser of claim 14 further including clamping means for securing said front cylindrically-shaped section of said support member within said barrel of said container, said clamping means comprising an annular ring adapted to fit over an outer cylindrical surface of said barrel and exert a compressive force on said barrel and said cylindrically-shaped section of said support member.

16. The dispenser of claim 9 wherein said flange of said container body is further defined as having formed in the rear surfaces of said semi-oval wing sections thereof a pair of symmetrical, crescent-shaped depressions, one in each wing section.

17. The dispenser of claim 16 wherein said support member is further defined as being a body having a front cylindrically-shaped section adapted to be insertably received into said rear circular opening of said barrel section of said container body, and a rear section having protuberances adapted to be insertably received within said crescent-shaped depressions in said rear surface of said rear flange wall of said container body.

18. The dispenser of claim 17 wherein said rear section of said support member is further defined as having in rear elevation view an oval shape similar to that of said rear flange of said container body.

19. The dispenser of claim 18 wherein said rear section of said support member is further defined as having protruding from the front surface thereof a pair of crescent-shaped lugs adapted to be insertably received within said crescent-shaped depressions in said rear surface of said container body.

20. The dispenser of claim 9 wherein said support member is further defined as comprising a body including means for attachment for attaching said body to the rear portion of said container body.

21. The dispenser of claim 20 wherein said attachment means is further defined as being adapted to fasten to said rear flange of said container body.

22. The dispenser of claim 21 wherein said attachment means is further defined as having formed therein a transversely disposed slot adapted to insertably receive said wings of said flange of said container barrel.

23. The dispenser of claim 22 wherein said support member is further defined as being a body of generally uniform thickness, said support member body having a generally flat rear wall provided therethrough with a central longitudinally disposed threaded hole, a generally flat front wall parallel to said rear wall, an upper wall having formed therein a wide, thin slot which extends downwards into said body and forms a space between said front and rear walls of the proper width and thickness to transversely slidably receive said wings of said rear flange of said container body, said front wall having formed therein a vertically disposed, generally rectangularly-shaped notch having parallel side edge walls and an arcuately curved, concave bottom edge wall adapted to conformally receive the outer cylindrical surface of said container body, said support member body having a lower wall provided with a narrow, then rectangular perforation communicating with said slot and adapted to insertably receive an outer end portion of a downwardly protruding flange wing of said container body.

24. The dispenser of claim 9 further including a flexible capillary fluid delivery tube attached to said hollow tubular front section of said barrel section of said container.

\* \* \* \* \*